United States Patent
Hinoue et al.

(10) Patent No.: US 6,268,515 B1
(45) Date of Patent: Jul. 31, 2001

(54) PROCESS FOR PRODUCING 3-HYDROXY-γ-BUTYROLACTONE DERIVATIVES

(75) Inventors: Kazumasa Hinoue; Yoshiro Furukawa, both of Amagasaki; Shigeo Katsumura, Takarazuka; Yoshikazu Takehira, Osaka, all of (JP)

(73) Assignee: Daiso Co., Ltd., Osaka (JP)

( * ) Notice: Subject to any disclaimer, the term of this patent is extended or adjusted under 35 U.S.C. 154(b) by 0 days.

(21) Appl. No.: 09/582,329

(22) PCT Filed: Dec. 7, 1998

(86) PCT No.: PCT/JP98/05518

§ 371 Date: Jun. 23, 2000

§ 102(e) Date: Jun. 23, 2000

(87) PCT Pub. No.: WO99/33816

PCT Pub. Date: Jul. 8, 1999

(30) Foreign Application Priority Data

Dec. 26, 1997  (JP) .................................................... 9-359452

(51) Int. Cl.[7] .................................................. C07D 307/06
(52) U.S. Cl. .............................................................. 549/313
(58) Field of Search ................................................ 549/313

(56) References Cited

U.S. PATENT DOCUMENTS 3,928,581 * 12/1975 Dahlberg et al. ..................... 424/180
4,056,672 * 11/1977 Dahlberg et al. ........................ 536/1

OTHER PUBLICATIONS

Buisson, D. et al, "New Chiral Building . . . Synthons", Tetrahedron Letters, vol. 28, No. 42 (1987), pp. 5033–5036.

* cited by examiner

Primary Examiner—Joseph K. McKane
Assistant Examiner—Sonya N. Wright
(74) Attorney, Agent, or Firm—Jacobson Holman, PLLC

(57) ABSTRACT

A process for preparing a 3-hydroxy-γ-butyrolactone derivative represented by the following formula (1):

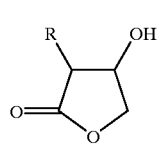

(1)

wherein R is $C_1$–$C_6$ alkyl, 3 to 6-membered cycloalkyl, aralkyl, 2-alkenyl, acyl, α-hydroxyalkyl, alkoxycarbonylalkyl or alkoxycarbonyl, which is characterized in treating 3-hydroxy-γ-butyrolactone with a metal salt of hexamethyldisilazane and then, reacting it with an electrophilic reagent, optionally in the presence of a reaction promoter.

9 Claims, No Drawings

PROCESS FOR PRODUCING 3-HYDROXY-γ-BUTYROLACTONE DERIVATIVES

This application is a 371 of PCT/JP98/05518 filed Dec. 7, 1998.

TECHNICAL FIELD

The present invention relates to a novel process for preparing a 3-hydroxy-γ-butyrolactone derivative which is useful as an intermediate in making medicines and agrochemicals.

BACKGROUND ART

A 3-hydroxy-γ-butyrolactone derivative is used as an intermediate in making medicines and agrochemicals. The known methods for preparing it are as follows: (i) The method by reacting 3-hydroxy-γ-butyrolactone with lithium diisopropylamide to form a dianion, followed by adding an alkylating agent (J. Org. Chem., 46, 4319 (1981)). (ii) The method of preparing a 3-hydroxy-γ-butyrolactone derivative by using 2-butenoic acid as a starting material (J. Chem. Res. (S), 274 (1996)).

DISCLOSURE OF INVENTION

The above known methods, however have following problems: The method (i) by reacting 3-hydroxy-γ-butyrolactone with lithium diisopropylamide to form a dianion, followed by adding an alkylating agent takes many hours in reaction and is low in yield. Furthermore, since hexamethylphosphoramide, which is carcinogenic, must be used as an additive, the method is not suitable for mass production.

The method (ii) of preparing a 3-hydroxy-γ-butyrolactone derivative by using 2-butenoic acid as a starting material needs to use a peracid not suitable for mass production and that requires many steps.

As a result of extensive investigation on an improved method for preparing a 3-hydroxy-γ-butyrolactone derivative, the present inventors have found that the 3-hydroxy-γ-butyrolactone derivative can be prepared by treating a metal salt of hexamethyldisilazane and 3-hydroxy-γ-butyrolactone as a starting material prior to reacting an electrophilic reagent such as an alkylating agent, and that a 3-hydroxy-γ-butyrolactone derivative can be prepared in good yield and in short times by undergoing the reaction with the electrophilic reagent in the presence of a reaction promoter.

The present invention relates to a novel process for preparing the 3-hydroxy-γ-butyrolactone derivative which is useful as an intermediate in making medicines and agrochemicals, namely to the process for preparing a 3-hydroxy-γ-butyrolactone derivative represented by the following formula (1):

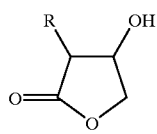

(1)

wherein R is $C_1$–$C_6$ alkyl, 3 to 6-membered cycloalkyl, aralkyl, 2-alkenyl, acyl, α-hydroxyalkyl, alkoxycarbonylalkyl or alkoxycarbonyl, which is characterized in treating 3-hydroxy-γ-butyrolactone with a metal salt of hexamethyldisilazane and then, reacting it with an electrophilic reagent, optionally in the presence of a reaction promoter.

The reaction of the present invention is shown in following reaction scheme:

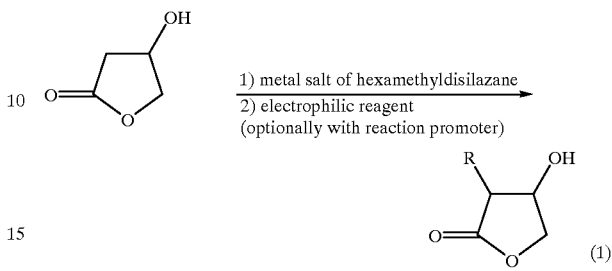

wherein R is the same as defined above.

The reaction is in detail explained as follows.

At first by reacting 3-hydroxy-γ-butyrolactone with a metal salt of hexamethyldisilazane under inert gas, such as argon or nitrogen under cooling to form a dianion. Then, the anionic compound is reacted with an electrophilic reagent, if necessary in the presence of a reaction promoter to prepare an objective compound (1).

Examples of a metal salt of hexamethyldisilazane are lithium hexamethyldisilazide, sodium hexamethyldisilazide or potassium hexamethyldisilazide, preferably lithium hexamethyldisilazide or sodium hexamethyldisilazide.

Amount of the metal salt to the substrate is 2–4 moles, preferably 2–2.5 moles.

Examples of the electrophilic reagent are alkyl halide-reagents, such as $C_1$–$C_6$ alkyl halide, 3 to 6-membered cycloalkyl halide, aralkyl halide or 2-alkenyl halide, aldehyde-reagents, ketone-reagents, ester-reagents, α-haloester-reagents, carbonate-reagents, or sulfonic acid ester-reagents, preferably alkyl halide-reagents.

Examples of the alkyl halide-reagent are alkyl chloride-reagents, such as methyl chloride, isopropyl chloride, cyclopropylmethyl chloride, cyclopentylmethyl chloride, cyclohexyl chloride, benzyl chloride, allyl chloride or methallyl chloride, alkyl bromide-reagents, such as methyl bromide, isopropyl bromide, cyclopropylmethyl bromide, cyclopentylmethyl bromide, cyclohexyl bromide, benzyl bromide, allyl bromide or methallyl bromide, or alkyl iodide-reagents, such as methyl iodide, isopropyl iodide, cyclopropylmethyl iodide, cyclopentylmethyl iodide, cyclohexyl iodide, benzyl iodide, allyl iodide or methallyl iodide. Especially preferable alkyl halide-reagents are methyl iodide, benzyl chloride, benzyl bromide, allyl chloride or allyl bromide.

Examples of the aldehyde-reagent are formaldehyde, acetaldehyde, benzaldehyde or cinnamaldehyde.

Examples of the ketone-reagent are acetone, diethyl ketone, vinylacetone or benzophenone.

Examples of the ester-reagent are methyl acetate, ethyl acetate, ethyl propionate or ethyl benzoate.

Examples of the α-halo ester-reagent are ethyl bromoacetate or ethyl 2-bromopropionate.

Examples of the carbonate-reagent are dimethyl carbonate, diethyl carbonate, diphenyl carbonate, methyl chlorocarbonate, ethyl chlorocarbonate or phenyl chlorocarbonate.

Examples of the sulfonic acid ester-reagent are p-toluenesulfonic acid ester, such as p-toluenesulfonic acid methyl ester, p-toluenesulfonic acid ethyl ester or p-toluenesulfonic acid glycidyl ester, methanesulfonic acid ester, such as methanesufonic acid methyl ester or methanesulfonic acid ethyl ester, or 3-nitrobenzenesulfonic acid ester such as 3-nitrobenzenesulfonic acid glycidyl ester.

Amount of the elecrophilic reagent is 1–4 moles to the substrate, preferably 1–2 moles.

Examples of a solvent used in this reaction are aprotic solvents, such as N,N-dimethylformamide or dimethyl sulfoxide, ethers, such as tetrahydrofuran, 1,4-dioxane, 1,2-dimethoxyethane, diglyme, triglyme, diethylene glycol monomethyl ether, halogeno compounds such as dichloromethane or 1,2-dichloroethane, or a mixture thereof. In view of going up yield, tetrahydrofuran and 1,2-dimethoxyethane are preferable solvents.

The reaction temperature is −100° C. to reflux temperature of the solvent, preferably −45° C. to room temperature.

When the electrophilic reagent is reacted, the reaction is promoted by adding a reaction promoter, and there is obtained the object compound (1) in a short time in good yield.

Examples of the reaction promoter are 1,3-dimethyl-2-imidazolidinone, 1,3-dimethyl-3,4,5,6-tetrahydro-2-pyrimidinone or tetramethylethylenediamine, preferably 1,3-dimethyl-2-imidazolidinone or 1,3-dimethyl-3,4,5,6-tetrahydro-2-pyrimidinone.

Amount of the promoter to the substrate is 1 to 20 moles, preferably 2 to 10 moles.

The starting materials used in the process of the present invention and the objective compounds (1) have asymmetric carbons and therefore, the optically active objective compound (1) is obtained by using an optically active compound as a starting material.

According to the process of the present invention, by using (S)-3-hydroxy-γ-butyrolactone, a (2S,3S)-3-hydroxy-γ-butylolactone derivative is predominantly prepared in a (2S,3S)-3-hydroxy-γ-butyrolactone derivative and a (2R,3S)-3-hydroxy-γ-butyrolactone derivative. On the other hand, by using (R)-3-hydroxy-γ-butyrolactone, a (2R,3R)-3-hydroxy-γ-butylolactone derivative is predomiantly prepared in a (2R,3R)-3-hydroxy-γ-butyrolactone derivative and a (2S,3R)-3-hydroxy-γ-butyrolactone derivative.

When 3-hydroxy-γ-butylolactone having highly optical purity is used, there is obtainable a 3-hydroxy-γ-butyrolactone derivative having highly optical purity without marked racemization on the way of the reaction.

EXAMPLE

The present invention is explained by following examples, but scope of the present invention should not be limited by these examples.

Example 1

Preparation of (2S,3S)-2-benzyl-3-hydroxy-γ-butyrolactone

Lithium hexamethyldisilazide (25 ml, 25 mmol) was loaded under argon gas in a reaction vessel. (S)-3-Hydroxy-γ-butyrolactone (1.012 g, 9.913 mmol) in THF (20 ml) was added thereto under cooling to −45° C. After stirring for 30 minutes at the same temperature, benzyl bromide (1.9 ml, 11.89 mmol) in THF (20 ml) was dropped thereto. After stirring for 4 hours at the same temperature, an aqueous saturated ammonium chloride was added to the reaction mixture and the mixture was extracted with ethyl acetate. The organic layer was washed with water and saturated brine, dried over magnesium sulfate, and condensed in vacuo. The residue was purified by silica gel chromatography to give (2S,3S)-2-benzyl-3-hydroxy-γ-butyrolactone (0.762 g, yield 40%).

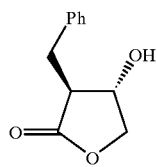

Example 2

Preparation of (2S,3S)-2-benzyl-3-hydroxy-γ-butyrolactone

Lithium hexamethyldisilazide (23 ml, 23 mmol) was loaded under argon gas in a reaction vessel. (S)-3-Hydroxyy-γ-butyrolactone (1.003 g, 9.825 mmol) in THF (20 ml) was added thereto under cooling to −45° C. After stirring for 30 minutes at the same temperature, benzyl bromide (1.4 ml, 11.79 mmol) and 1,3-dimethyl-2-imidazolidinone (2.9 ml) in THF (20 ml) was dropped thereto. After stirring for 30 minutes at the same temperature, an aqueous saturated ammonium chloride was added to the reaction mixture and the mixture was extracted with ethyl acetate. The organic layer was washed with water and saturated brine, dried over magnesium sulfate, and condensed in vacuo. The residue was purified by silica gel chromatography to give (2S,3S)-2-benzyl-3-hydroxy-γ-butyrolactone (1.513 g, yield 80%).

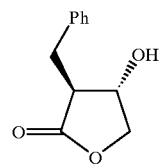

Example 3

Preparation of (2S,3S)-2-methyl-3-hydroxy-γ-butyrolactone

Lithium hexamethyldisilazide (23 ml, 23 mmol) was loaded under argon gas in a reaction vessel. (S)-3-Hydroxy-γ-butyrolactone (1.007 g, 9.864 mmol) in THF (20 ml) was added thereto under cooling to −45° C. After stirring for 30 minutes at the same temperature, methyl iodide (0.74 ml, 11.84 mmol) and 1,3-dimethyl-2-imidazolidinone (2.7 ml) in THF (20 ml) was dropped thereto. After stirring for 30 minutes at the same temperature, an aqueous saturated ammonium chloride was added to the reaction mixture and the mixture was extracted with ethyl acetate. The organic layer was washed with water and saturated brine, dried over magnesium sulfate, and condensed in vacuo. The residue was purified by silica gel chromatography to give (2S,3S)-2-methyl-3-hydroxy-γ-butyrolactone (0.813 g, yield 71%).

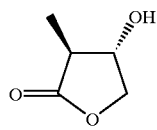

Example 4

Preparation of (2S,3S)-2-allyl-3-hydroxy-γ-butyrolactone

Lithium hexamethyldisilazide (5.1 ml, 5.1 mmol) was loaded under argon gas in a reaction vessel. (S)-3-Hydroxy- γ-butyrolactone (0.250 g, 2.449 mmol) in THF (5 ml) was added thereto under cooling to −45° C. After stirring for 30 minutes at the same temperature, allyl chloride (0.24 ml, 2,94 mmol) and 1,3-dimethyl-2-imidazolidinone (0.7 ml) in THF (5 ml) was dropped thereto. After stirring for 30 minutes at the same temperature, an aqueous saturated ammonium chloride was added to the reaction mixture and the mixture was extracted with ethyl acetate. The organic layer was washed with water and saturated brine, dried over magnesium sulfate, and condensed in vacuo. The residue was purified by silica gel chromatography to give (2S,3S)-2-allyl-3-hydroxy-γ-butyrolactone (0.261 g, yield 75%).

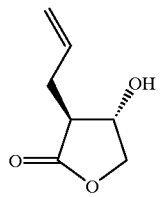

Comparative Example

Diisopropylamine (2.7 ml, 19.59 mmol) and 1.6 M of n-butyllithium-hexane solution (12.2 ml, 19.59 mmol) were added to THF (30 ml) under argon gas at 0° C. After stirring for 15 minutes, the solution was cooled to −45° C. Then, (S)-3-hydroxy-γ-butyrolactone (1 g, 9.794 mmol) in THF (20 ml) was added thereto. After stirring for 30 minutes at −45° C., benzyl bromide (1.4 ml, 11.75 mmol) and 1,3-dimethyl2-imidazolidinone (2.9 ml) in THF (20 ml) were added thereto. After stirring for 3 hours at the same temperature, an aqueous saturated ammonium chloride was added to the reaction mixture and the mixture was extracted with ethyl acetate. The organic layer was washed with water and saturated brine, dried over magnesium sulfate, and condensed in vacuo. The residue was purified by silica gel chromatography to give (2S,3S)-2-benzyl-3-hydroxy-γ-butyrolactone (0.577 g, yield 31%).

What is claimed is:

1. A process for preparing a 3-hydroxy-γ-butyrolactone of formula (1):

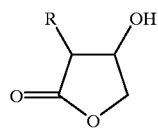

(1)

wherein R is $C_1$–$C_6$ alkyl, 3- to 6-membered cycloalkyl, aralkyl, 2-alkenyl, acyl, α-hydroxyalkoxyalkyl, alkoxycarbonylalkyl or alkoxycarbonyl. by reacting 3-hydroxy-γ-butyolactone with a metal salt of hexamethyldisilazane, and then reacting it with an electrophilic reagent.

2. The process of claim 1 wherein the electrophilic reagent is reacted in the presence of a reaction promoter.

3. The process of claim 1 wherein the metal salt of hexamethyldisilazane is lithium hexamethyldisilazide, sodium hexamethyldisilazide, or potassium hexamethyldisilzide.

4. The process of claim 1 wherein the electrophilic reagent is an alkyl halide reagent.

5. The process of claim 4 wherein the alkyl halide reagent is methyl iodide, benzyl chloride, benzyl bromide, allyl chloride, or allyl bromide.

6. The process of claim 2 wherein the reaction promoter is 1,3-dimethyl-2-imidazolidone, 1,3-dimethyl-3,4,5,6-tetrahydro-2-pyrimidinone, or tetramethylethylenediamine.

7. The process of claim 1 wherein an optically active 3-hydroxy-γ-butyrolactone of formula (1) is obtained by using optically active 3-hydroxy-γ-butyrolactone as the starting 3-hydroxy-γ-butyrolactone.

8. The process of claim 1 wherein a (2S,3S)-3-hydroxy-γ-butyrolactone of formula (1) is obtained by using (S)-3-hydroxy-γ-butyrolactone as the starting 3-hydroxy-γ-butyrolactone.

9. The process of claim 1 wherein a (2R,3R)-3-hydroxy-γ-butyrolactone of formula (1) is obtained by using (R)-3-hydroxy-γ-butyrolactone as the starting 3-hydroxy-γ-butyrolactone.

* * * * *